United States Patent
Sullivan

(10) Patent No.: US 12,337,185 B1
(45) Date of Patent: Jun. 24, 2025

(54) DETECTING SHOCKABLE POLYMORPHIC VENTRICULAR TACHYCARDIA

(71) Applicant: West Affum Holdings Designated Activity Company, Dublin (IE)

(72) Inventor: Joseph L. Sullivan, Kirkland, WA (US)

(73) Assignee: West Affum Holdings Designated Activity Company, Dublin (IE)

( * ) Notice: Subject to any disclaimer, the term of this patent is extended or adjusted under 35 U.S.C. 154(b) by 0 days.

(21) Appl. No.: 17/148,101

(22) Filed: Jan. 13, 2021

Related U.S. Application Data

(60) Provisional application No. 62/989,668, filed on Mar. 14, 2020.

(51) Int. Cl.
| | | |
|---|---|---|
| *A61N 1/39* | (2006.01) | |
| *A61B 5/024* | (2006.01) | |
| *A61B 5/363* | (2021.01) | |
| *A61B 5/366* | (2021.01) | |
| *A61N 1/362* | (2006.01) | |

(52) U.S. Cl.
CPC ............ *A61N 1/3904* (2017.08); *A61B 5/024* (2013.01); *A61B 5/363* (2021.01); *A61B 5/366* (2021.01)

(58) Field of Classification Search
None
See application file for complete search history.

(56) References Cited

U.S. PATENT DOCUMENTS

| | | |
|---|---|---|
| 3,724,355 A | 4/1973 | Unger |
| 3,724,455 A | 4/1973 | Unger |
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |

(Continued)

FOREIGN PATENT DOCUMENTS

| | | |
|---|---|---|
| DE | 102005060985 A1 | 6/2007 |
| EP | 2305110 A1 | 4/2011 |

(Continued)

OTHER PUBLICATIONS

Keller, Dagmar I. "Wide-complex tachycardia". Cardiovascular Medicine. 2018; 21(4):90-96 (Year: 2018).*

(Continued)

*Primary Examiner* — Erica S Lee
(74) *Attorney, Agent, or Firm* — POLSINELLI PC

(57) ABSTRACT

In one embodiment, a method to diagnose a heart condition by a wearable cardioverter defibrillator is described. The method includes obtaining a signal from the at least one sensor and analyzing the signal from the at least one sensor into usable data. The method including calculating a measured heart rate and a consistency metric from the usable data. The method further including determining when the measured heart rate satisfies a heart rate threshold and determining when the consistency metric satisfies a consistency threshold. The method including diagnosing a slow PVT episode based at least in part on the heart rate threshold and consistency threshold being satisfied.

21 Claims, 7 Drawing Sheets

(56) References Cited

U.S. PATENT DOCUMENTS

| | | |
|---|---|---|
| 5,228,449 A | 7/1993 | Christ et al. |
| 5,348,008 A | 9/1994 | Born et al. |
| 5,353,793 A | 10/1994 | Born |
| RE34,800 E | 11/1994 | Hutchins |
| 5,394,892 A | 3/1995 | Kenny |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,450,942 B1 | 9/2002 | Lapanashvili et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov et al. |
| 7,212,850 B2 | 5/2007 | Prystowsky et al. |
| 7,559,902 B2 | 7/2009 | Ting et al. |
| 7,587,237 B2 | 9/2009 | Korzinov et al. |
| 7,753,759 B2 | 7/2010 | Pintor et al. |
| 7,865,238 B2 | 1/2011 | Brink |
| 7,870,761 B2 | 1/2011 | Valentine et al. |
| 7,894,894 B2* | 2/2011 | Stadler ............. A61N 1/3956 607/4 |
| 7,907,996 B2 | 3/2011 | Prystowsky et al. |
| 7,941,207 B2 | 5/2011 | Korzinov |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 11,471,693 B1 | 10/2022 | Sullivan |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0243201 A1* | 10/2008 | Bocek ............. A61N 1/39622 607/4 |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0216446 A1* | 8/2015 | Bukhman ............. A61B 5/061 600/521 |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0228718 A1* | 8/2016 | Koop ............. A61B 5/35 |
| 2016/0235998 A1* | 8/2016 | Warren ............. A61N 1/3987 |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |

(56) References Cited

U.S. PATENT DOCUMENTS

| | | | |
|---|---|---|---|
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0282823 A1* | 9/2019 | Freeman | A61N 1/3968 |
| 2019/0321650 A1 | 10/2019 | Raymond et al. | |
| 2019/0374783 A1* | 12/2019 | Zhang | A61N 1/3925 |

FOREIGN PATENT DOCUMENTS

| | | |
|---|---|---|
| JP | 4320257 B2 | 8/2009 |
| JP | 2014526282 A | 10/2014 |
| JP | 5963767 B2 | 8/2016 |
| WO | 1998039061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |

OTHER PUBLICATIONS

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Zoll, LifeVest, Proven protection from Sudden Cardiac Death, 2017, Pittsburgh PA, USA, 4 pages.

International Search Report and Written Opinion for PCT Application No. PCT/US2015/051726, dated May 20, 2016, European Patent Office, Rijswijk, (11 pages).

* cited by examiner

DETECTING SHOCKABLE POLYMORPHIC VENTRICULAR TACHYCARDIA

CROSS REFERENCE TO RELATED PATENT APPLICATIONS

This patent application claims benefit of U.S. Provisional Patent Application No. 62/989,668 filed Mar. 14, 2020 and is incorporated herein by reference in their entirety for all purposes.

BACKGROUND

When people suffer from some types of heart arrhythmias, in some instances, blood flow to various parts of the body may be reduced. Some arrhythmias can result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people may include patients who have had a heart attack or a prior SCA episode. A frequent recommendation for these people is to receive an Implantable Cardioverter Defibrillator (ICD). The ICD is surgically implanted in the chest, and continuously monitors the patient's intracardiac electrogram (IEGM). If certain types of heart arrhythmias are detected, then the ICD delivers an electric shock through the heart.

As a further precaution, people who have been identified to have an increased risk of a SCA are sometimes given a Wearable Cardioverter Defibrillator (WCD) system to wear until an ICD is implanted. Early versions of such systems were called wearable cardiac defibrillator systems. A WCD system typically includes a harness, vest, belt, or other garment that the patient wears. The WCD system further includes electronic components, such as a defibrillator and electrodes, coupled to the harness, vest, or another garment. When the patient wears the WCD system, the electrodes may electrically contact the patient's skin, and aid in sensing the patient's electrocardiogram (ECG). If a shockable heart arrhythmia (e.g., ventricular fibrillation or VF) is detected from the ECG, then the defibrillator delivers an appropriate electric shock through the patient's body, and thus through the heart. The delivered shock may restart the patient's heart and save the patient's life.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes instances and examples of cardiac monitoring systems (e.g., WCD systems), devices, systems, storage media that may store programs, and methods.

In one embodiment, a method to diagnose a heart condition by a wearable cardioverter defibrillator (WCD) is described. The method includes obtaining a signal from the at least one sensor and analyzing the signal from the at least one sensor into QRS complexes. The method also includes determining a width of QRS complexes and determining a heart rate from the width of the QRS complexes. Next the method diagnoses a slow PVT episode based at least in part on the heart rate and QRS complexes.

In some embodiment, the heart rate may be between 120 and 170 beats per minute (BPM) and the QRS complexes may be wider than 120 microseconds (ms). In some embodiments, the method may issue a shock command based at least in part on the slow polymorphic ventricular tachycardia (PVT) episode. In some embodiments, the method may issue a delay shock command based at least in part on the slow PVT episode and monitor the heart rate based at least in part on the delay shock command for a predetermined time period.

In some embodiments, the method may issue a shock command after the predetermined time period has lapsed when the slow PVT episode is present. In some embodiments, the method may store the slow PVT episode in memory. In some embodiments, the method may calculate a QRS consistency metric for a patient and compare a QRS width to the QRS consistency metric. The method may also calculate a similarity between the QRS width and the QRS consistency metric and may issue a shock command when the similarity is above a predetermined threshold.

In another embodiment, a wearable cardiac defibrillator (WCD) system for monitoring health of a patient wearing the WCD system is described. The system includes at least one sensor positioned to gather data about the patient and one or more memories. The one or more memories are configured to store patient data and one or more processors configured to cause the system to obtain a signal from the at least one sensor and analyze the signal from the at least one sensor into QRS complexes. The processor is also configured to determine a width of QRS complexes, determine a heart rate from the width of the QRS complexes, and diagnose a slow PVT episode based at least in part on the heart rate and QRS complexes.

In some embodiments, the heart rate may be between 120 and 170 BPM and the QRS complexes may be wider than 120 ms. In some embodiments, the processor may be configured to issue a shock command based at least in part on the slow PVT episode. In some embodiments, the processor may be configured to issue a delay shock command based at least in part on the slow PVT episode and monitor the heart rate based at least in part on the delay shock command for a predetermined time period. In some embodiments, the processor may be configured to issue a shock command after the predetermined time period has lapsed when the slow PVT episode is present.

In some embodiments, the processor may be configured to store the slow PVT episode in the one or more memory. In some embodiments, the processor may be configured to calculate a QRS consistency metric for a patient and compare a QRS width to the QRS consistency metric. The processor may calculate a similarity between the QRS width and the QRS consistency metric and issue a shock command when the similarity is above a predetermined threshold.

In another embodiment, a method to diagnose a heart condition by a wearable cardioverter defibrillator is described. The method includes obtaining a signal from the at least one sensor and analyzing the signal from the at least one sensor into usable data. The method including calculating a measured heart rate and a consistency metric from the usable data. The method further including determining when the measured heart rate satisfies a heart rate threshold and determining when the consistency metric satisfies a consistency threshold. The method including diagnosing a slow PVT episode based at least in part on the heart rate threshold and consistency threshold being satisfied.

In some embodiments, the method may include issuing a delay shock command based at least in part on the slow PVT episode and monitoring the heart rate based at least in part on the delay shock command for a predetermined time period. The method may also include issuing a shock command based at least in part on the slow PVT episode. In some instances, the first consistency metric may be an SVT discriminator consistency metric for a patient. In some embodiments, the method may include calculating a SVT discriminator from the usable data and comparing the SVT discriminator to the SVT discriminator consistency metric. The method may calculate a similarity between the SVT discriminator and the SVT discriminator consistency metric and issue a shock command when the similarity is above a predetermined threshold. In some embodiments, the method may store the slow PVT episode in memory.

BRIEF DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
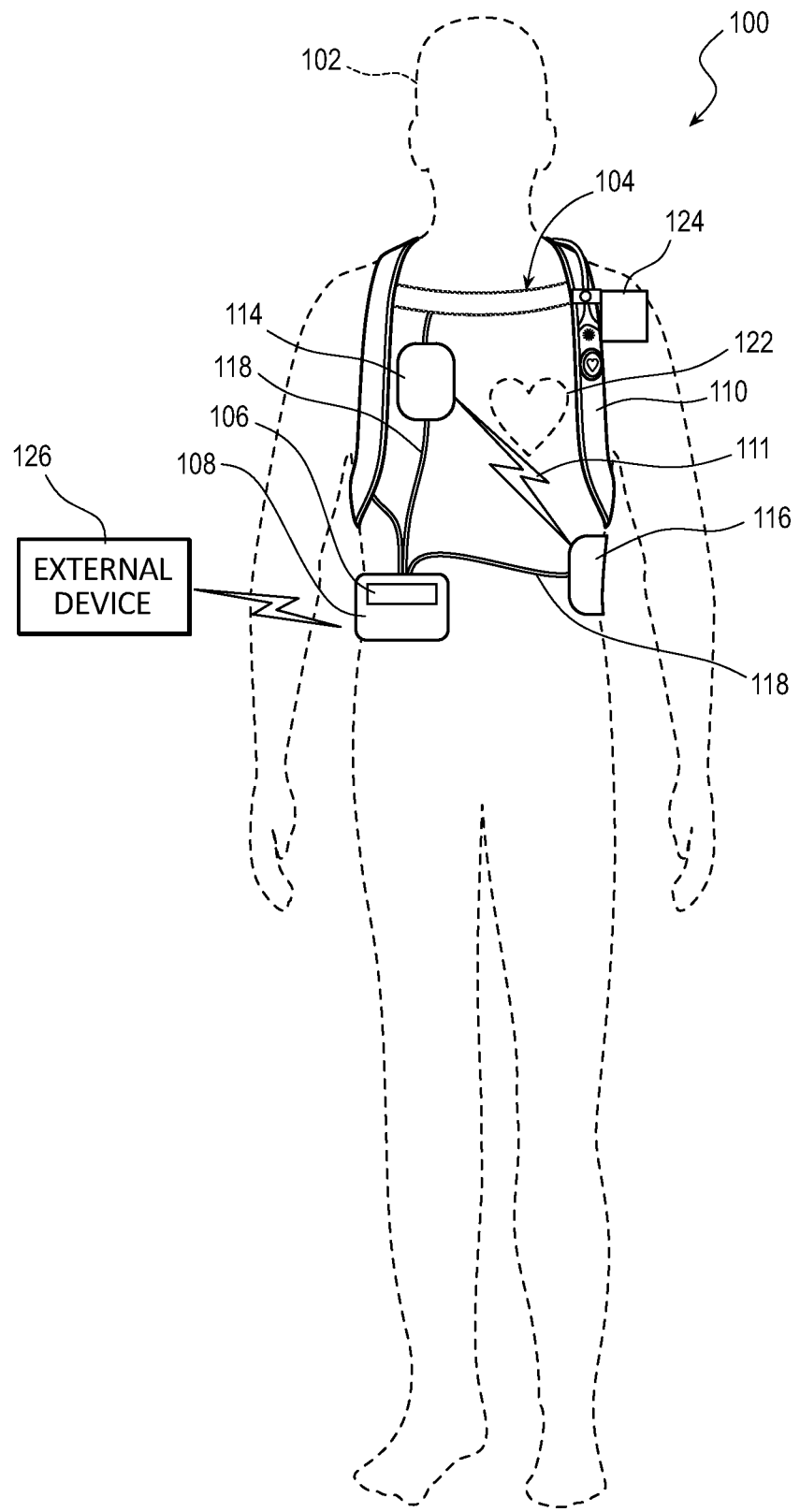
FIG. 1 is a diagram of a sample WCD system in accordance with exemplary embodiments described herein.

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCDs) are worn by patients at risk for sudden cardiac arrest. Sudden cardiac arrest may include conditions such as polymorphic ventricular tachycardia (PVT). PVT can be treated using defibrillators, including WCDs, by providing a shock to the patient.

Defibrillators are typically programmed with a heart rate cutoff. If a heart rate registers below the cutoff, the defibrillator will register a normal heart rate and determine no shock is needed. However, in some patients PVT may occur with heart rates below the predetermined cutoff. The present disclosure provides embodiments of defibrillators that can detect PVT below the heart rate cutoff and provide the patient with shock therapy.

Clinically, patients experiencing ventricular fibrillation (VF) and PVT need to be shocked rapidly or they may suffer severe consequences. VF typically exhibits a high heart rate, approximately 200 beats per minute (BPM) or more. PVT rates vary greatly, but they can occasionally be as slow as approximately 120 BPM. Regardless of the heart rate, these rhythms are non-perfusing and should be shocked quickly.

Heart rate is an imperfect indicator of shock conditions. In a typical defibrillator, the heart rate cutoff for ventricular tachycardia (VT) is typically greater than 120 BPM. For example, in some defibrillators the heart rate cutoff is set between approximately 150 BPM and approximately 180 BPM. As a result, PVT with a heart rate below the cutoff is not shocked by such defibrillators. For example, in some embodiments, VF is a shockable condition and typically presents with a high heart rate, in excess of approximately 200 BPM. However, VF may occur at slower heart rates. Additionally, some types of VT present shockable conditions. For example, patients experiencing VF and PVT may need to be shocked rapidly to prevent dire circumstances. VF typically exhibits a high heart rate, approximately 200 BPM or higher. In contrast, PVT rates vary greatly, but, in some instances, PVT may present itself at heart rates as low as 120. Regardless of the heart rate, these rhythms are non-perfusing and should be shocked quickly.

Monomorphic VT (MVT) may be more difficult to detect. Without other information, heart rate is used to assess when MVT presents a shockable condition. In some instances, MVT between approximately 150 BPM and 170 BPM may be tolerable, while higher rates may be a shockable condition. In some instances, MVT may self-terminate. Therefore, MVT presents an abnormal situation and does not always need to be shocked. If MVT is detected, the system may wait a predetermined time period to MVT to self-terminate prior to issuing a shock decision.

Another condition, supraventricular tachycardia (SVT), may have low heart rates, less than approximately 100 BPM. However, in some instances, SVT may present at a heart rate higher than 200 BPM. Regardless, SVT is generally well tolerated by patients, and typically does not need to be shocked by a defibrillator.

FIG. 1 illustrates a system 100 with a patient 102 wearing an example of a WCD system 104 according to embodiments described herein. In some embodiments, the WCD system 104 may include one or more communication devices 106, a support structure 110, and an external defibrillator 108 connected to two or more defibrillation electrodes 114, 116, among other components.

The support structure 110 may be worn by the patient 102. The patient 102 may be ambulatory, meaning the patient 102 can walk around and is not necessarily bed-ridden while wearing the wearable portion of the WCD system 104. While the patient 102 may be considered a "user" of the WCD system 104, this is not a requirement. For instance, a user of the WCD system 104 may also be a clinician such as a doctor, nurse, emergency medical technician (EMT) or other similarly tasked individual or group of individuals. In some cases, a user may even be a bystander. The particular context of these and other related terms within this description should be interpreted accordingly.

In some embodiments, the support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso 112 of the patient 102. A second component may rest more towards a patient's hips, whereby the second component may be positioned such that the patient's hips support the heavier components of the WCD system 104. In some embodiments, the heavier components of the WCD system 104 may be carried via a shoulder strap or may be kept close to the patient 102 such as in a cart, bag, stroller, wheelchair, or other vehicle.

The external defibrillator 108 may be coupled to the support structure 110 or may be carried remotely from the patient 102. The external defibrillator 108 may be triggered to deliver an electric shock to the patient 102 when patient 102 wears the WCD system 104. For example, if certain thresholds are exceeded or met, the external defibrillator 108 may engage and deliver a shock to the patient 102.

The defibrillation electrodes 114, 116 can be configured to be worn by patient 102 in a number of ways. For instance, the defibrillator 108 and the defibrillation electrodes 114, 116 can be coupled to the support structure 110 directly or indirectly. For example, the support structure 110 can be configured to be worn by the patient 102 to maintain at least one of the electrodes 114, 116 on the body of the patient 102, while the patient 102 is moving around, etc. The electrodes 114, 116 can be thus maintained on the torso 112 by being attached to the skin of patient 102, simply pressed against the skin directly or through garments, etc. In some embodiments, the electrodes 114, 116 are not necessarily pressed against the skin but becomes biased that way upon sensing a condition that could merit intervention by the WCD system 104. In addition, many of the components of defibrillator 108 can be considered coupled to support structure 110 directly, or indirectly via at least one of defibrillation electrodes 114, 116.

The WCD system 104 may defibrillate the patient 102 by delivering an electrical charge, pulse, or shock 111 to the patient 102 through a series of electrodes 114, 116 positioned on the torso 112. For example, when defibrillation electrodes 114, 116 are in good electrical contact with the torso 112 of patient 102, the defibrillator 108 can administer, via electrodes 114, 116, a brief, strong electric pulse 111 through the body. The pulse 111 is also known as shock, defibrillation shock, therapy, electrotherapy, therapy shock, etc. The pulse 111 is intended to go through and restart heart 122, in an effort to save the life of patient 102. The pulse 111 can further include one or more pacing pulses of lesser magnitude to pace heart 122 if needed. The electrodes 114, 116 may be electrically coupled to the external defibrillator 108 via a series of electrode leads 118. The defibrillator 108 may administer an electric shock 111 to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116.

In some embodiments, the WCD system 104 may also include either an external or internal monitoring device or some combination thereof. FIG. 1 displays an external monitoring device 124 which may also be known as an outside monitoring device. The monitoring device 124 may monitor at least one local parameter. Local parameters may include a physical state of the patient 102 such as ECG, movement, heartrate, pulse, temperature, and the like. Local parameters may also include a parameter of the WCD 104, environmental parameters, or the like. The monitoring device 124 may be physically coupled to the support structure 110 or may be proximate the support structure 110. In either location, the monitoring device 124 is communicatively coupled with other components of the WCD 104.

For some of these parameters, the device 124 may include one or more sensors or transducers. Each one of such sensors can be configured to sense a parameter of the patient 102, and to render an input responsive to the sensed parameter. In some embodiments, the input is quantitative, such as values of a sensed parameter; in other embodiments, the input is qualitative, such as informing whether or not a threshold is crossed. In some instances, these inputs about the patient 102 are also referred to herein as patient physiological inputs and patient inputs. In some embodiments, a sensor can be construed more broadly, as encompassing many individual sensors.

In some embodiments, a communication device 106 may enable the patient 102 to interact with, and garnish data from, the WCD system 104. The communication device 106 may enable a patient or third party to view patient data, dismiss a shock if the patient is still conscious, turn off an alarm, and otherwise engage with the WCD system 104. In some instances, the communication device 106 may transfer or transmit information include patient data to a third-party data server such as a cloud server or a blockchain server. In some embodiments, the communication device 106 may be a separable part of an external defibrillator 108. For example, the communication device 106 may be a separate device coupled to the external defibrillator 108. In some embodiments, the communication device 106 may be wired or wirelessly linked to the external defibrillator 108 and may be removable from the defibrillator 108. In other embodiments, the communication device 106 may form an inseparable assembly and share internal components with the external defibrillator 108. In some embodiments, the WCD system 104 may include more than one communication device 106. For example, the defibrillator 108 may include components able to communicate to the patient and the WCD system 104 may include a separate communication device 106 remote form the defibrillator 108.

In some embodiments, the defibrillator 108 may connect with one or more external devices 126. For example, as shown in FIG. 1, the defibrillator 108 may connect to various external devices 126 such as a the cloud, a remote desktop, a laptop, a mobile device, or other external device using a network such as the Internet, local area networks, wide area networks, virtual private networks (VPN), other communication networks or channels, or any combination thereof.

In embodiments, one or more of the components of the exemplary WCD system 104 may be customized for the patient 102. Customization may include a number of aspects including, but not limited to, fitting the support structure 110 to the torso 112 of patient 102; baseline physiological parameters of patient 102 can be measured, such as the heart rate of patient 102 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and the like. Moreover, a programming interface can be made according to embodiments, which receives such measured values of baseline physiological parameters. Such a programming interface may input automatically in the WCD system these, along with other data.

Figure 2:
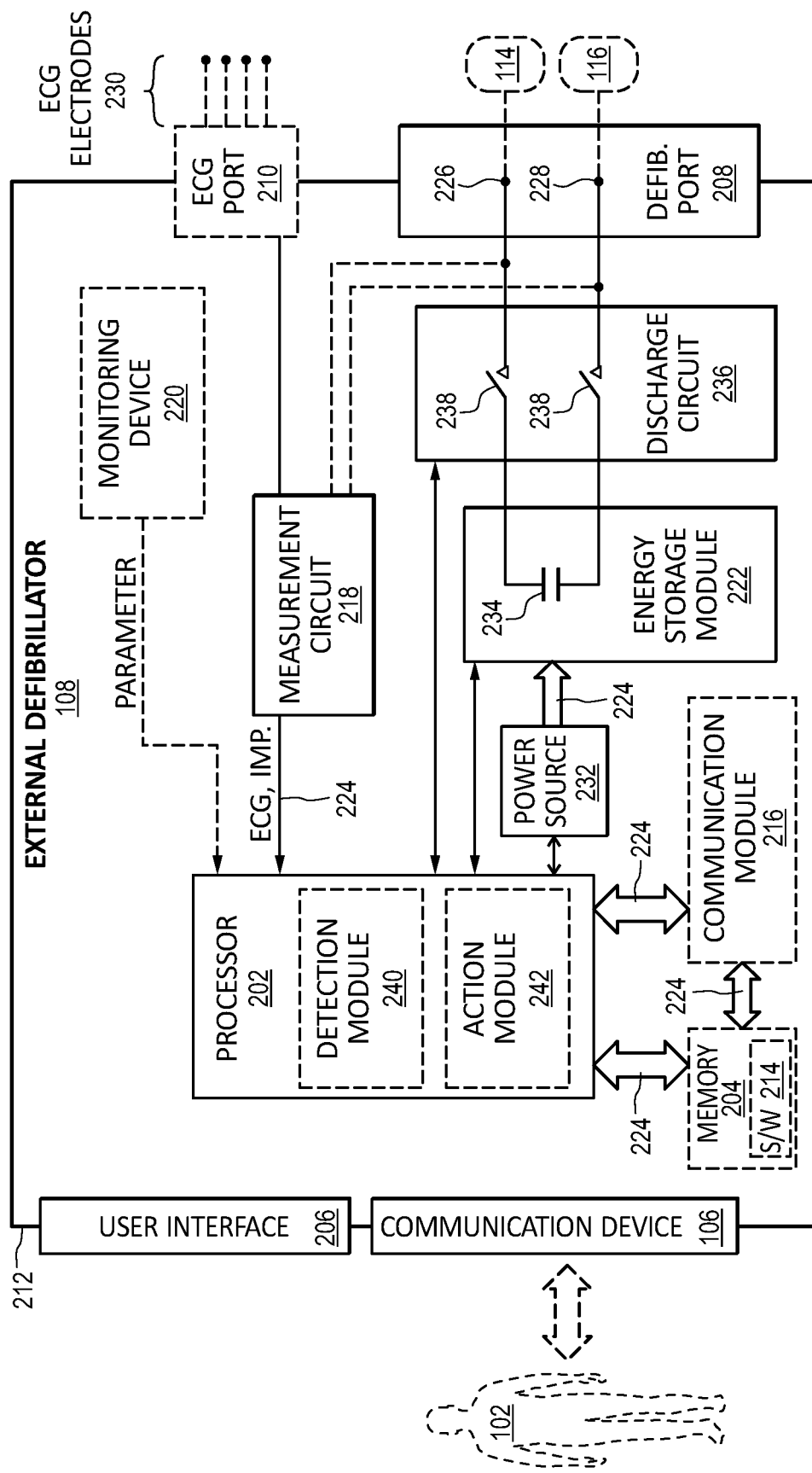
FIG. 2 is a block diagram of an example defibrillator in accordance with exemplary embodiments described herein.

FIG. 2 is a diagram displaying various components of an example external defibrillator 108. The external defibrillator 108 may be an example of the defibrillator 108 described with reference to FIG. 1. The components shown in FIG. 2 may be contained within a single unit or may be separated amongst two or more units in communication with each other. The defibrillator 108 may include a communication device 106, processor 202, memory 204, defibrillation port 208, and ECG port 210, among other components. In some embodiments, the components are contained within a housing 212 or casing. The housing 212 may comprise a hard shell around the components or may comprise a softer shell for increased patient comfort.

The communication device 106, processor 202, memory 204 (including software/firmware code (SW) 214), defibrillation port 208, ECG port 210, communication module 216, measurement circuit 218, monitoring device 220, and energy storage module 222 may communicate, directly or indirectly, with one another via one or more buses 224. The one or more buses 224 may allow data communication between the elements and/or modules of the defibrillator 108.

The memory 204 may include random access memory (RAM), read only memory (ROM), flash RAM, and/or other types. The memory 204 may store computer-readable, computer-executable software/firmware code 214 including instructions that, when executed, cause the processor 202 to perform various functions (e.g., determine shock criteria, determine heart rate, issue shock command, etc.). In some embodiments, the processor 202 may include an intelligent hardware device, e.g., a central processing unit (CPU), a microcontroller, an application-specific integrated circuit (ASIC), etc.

In some embodiments, the memory 204 can contain, among other things, the Basic Input-Output system (BIOS) which may control basic hardware and/or software operations such interactions and workings of the various components of the defibrillator 108, and in some embodiments, components external to the defibrillator 108. For example, the memory 204 may contain various modules to implement the workings of the defibrillator 108 and other aspects of the present disclosure.

In some embodiments, the defibrillator 108 may include a user interface 206. The user interface 406 may be in addition to or part of the communication device 106. The user interface 406 may display an ECG of the patient, a status of the defibrillator 108, a status of a charge (e.g. a battery charge or an energy storage module), and the like.

In some embodiments, the defibrillator 108 may include a defibrillation port 208. The defibrillation port 208 may comprise a socket, opening, or electrical connection in the housing 212. In some instances, the defibrillation port 208 may include two or more nodes 226, 228. The two or more nodes 226, 228 may accept two or more defibrillation electrodes (e.g. defibrillation electrodes 114, 116, FIG. 1). The nodes 226, 228 may provide an electrical connection between the defibrillation electrodes 114, 116 and the defibrillator 108. The defibrillation electrodes 114, 116 may plug into the two or more nodes 226, 228 via one or more leads (e.g. leads 118), or, in some instances, the defibrillation electrodes 114, 116 may be hardwired to the nodes 226, 228. Once an electrical connection is established between the defibrillation port 208 and the electrodes 114, 116, the defibrillator 108 may be able to deliver an electric shock to the patient 102.

In some embodiments, the defibrillator 108 may include an ECG port 210 in the housing 212. The ECG port 210 may accept one or more ECG electrodes 230 or ECG leads. In some instances, the ECG electrodes 230 sense a patient's ECG signal. For example, the ECG electrodes 230 may record electrical activity generated by heart muscle depolarization. The ECG electrodes 230 may utilize 4-leads to 12-leads or multichannel ECG, or the like. The ECG electrodes 230 may connect with the patient's skin.

In some embodiments, the defibrillator 108 may include a measurement circuit 218. The measurement circuit 218 may be in communication with the ECG port 210. For example, the measurement circuit 218 may receive physiological signals from ECG port 210. The measurement circuit 218 may additionally or alternatively receive physiological signals via the defibrillation port 208 when defibrillation electrodes 114, 116 are attached to the patient 102. The measurement circuit 218 may determine a patient's ECG signal from a difference in voltage between the defibrillation electrodes 114, 116.

In some embodiments, the measurement circuit 218 may monitor the electrical connection between the defibrillation electrodes 114, 116 and the skin of the patient 102. For example, the measurement circuit 218 can detect impedance between electrodes 114, 116. The impedance may indicate the effective resistance of an electric circuit. An impedance calculation may determine when the electrodes 114, 116 have a good electrical connection with the patient's body.

In some embodiments, the defibrillator 108 may include an internal monitoring device 220 within the housing 212. The monitoring device 220 may monitor at least one local parameter. Local parameters may include physical state of the patient such as ECG, movement, heartrate, pulse, temperature, and the like. Local parameters may also include a parameter of the WCD system (e.g. WCD 104, FIG. 1), defibrillator 108, environmental parameters, or the like.

In some embodiments, the WCD system 104 may include an internal monitoring device 220 and an external monitoring device (e.g. external monitoring device 124). If both monitoring devices 124, 220 are present, the monitoring devices 124, 220 may work together to parse out specific parameters depending on position, location, and other factors. For example, the external monitoring device 124 may monitor environmental parameters while the internal monitoring device 220 may monitor patient and system parameters.

In some embodiments, the defibrillator 108 may include a power source 232. The power source 232 may comprise a battery or battery pack, which may be rechargeable. In some instances, the power source 232 may comprise a series of different batteries to ensure the defibrillator 108 has power. For example, the power source 232 may include a series of rechargeable batteries as a prime power source and a series of non-rechargeable batteries as a secondary source. If the patient 102 is proximate an AC power source, such as when sitting down, sleeping, or the like, the power source 232 may include an AC override wherein the power source 232 draws power from the AC source.

In some embodiments, the defibrillator 108 may include an energy storage module 222. The energy storage module 222 may store electrical energy in preparation or anticipation of providing a sudden discharge of electrical energy to the patient. In some embodiments, the energy storage module 222 may have its own power source and/or battery pack. In other embodiments, the energy storage module 222 may pull power from the power source 232. In still further embodiments, the energy storage module 222 may include one or more capacitors 234. The one or more capacitors 234 may store an electrical charge, which may be administered to the patient. The processor 202 may be communicatively coupled to the energy storage module 222 to trigger the amount and timing of electrical energy to provide to the defibrillation port 208 and, subsequently, the patient 102.

In some embodiments, the defibrillator 108 may include a discharge circuit 236. The discharge circuit 236 may control the energy stored in the energy storage module 222. For example, the discharge circuit 236 may either electrical couple or decouple the energy storage module 222 to the defibrillation port 208. The discharge circuit 236 may be communicatively coupled to the processor 202 to control when the energy storage module 222 and the defibrillation port 208 should or should not be coupled to either administer or prevent a charge from emitting from the defibrillator 108. In some embodiments, the discharge circuit 236 may include on or more switches 238. In further embodiments, the one or more switches 238 may include an H-bridge.

In some embodiments, the defibrillator 108 may include a communication module 216. The communication module 216 may establish one or more communication links with either local hardware and/or software to the WCD system 104 and defibrillator 108 or to remote hardwire separate from the WCD system 104. In some embodiments, the communication module 216 may include one or more antennas, processors, and the like. The communication module 216 may communicate wirelessly via radio frequency, electromagnetics, local area networks (LAN), wide area networks (WAN), virtual private networks (VPN), RFID, Bluetooth, cellular networks, and the like. The communication module 216 may facilitate communication of data and commands such as patient data, episode information, therapy attempted, CPR performance, system data, environmental data, and so on.

In some embodiments, the processor 202 may execute one or more modules. For example, the processor 202 may execute a detection module 240 and/or an action module 242. The detection module 240 may be a logic device or algorithm to determine if any or a variety of thresholds are exceeded which may require action of the defibrillator 108. For example, the detection module 240 may receive and interpret all of the signals from the ECG port 210, the defibrillation port 208, the monitoring device 220, an external monitoring device, and the like. The detection module 240 may process the information to ensure the patient is still conscious and healthy. If any parameter indicates the patient 102 may be experiencing distress or indicating a cardiac episode, the detection module 240 may activate the action module 242.

The action module 242 may receive data from the detection module 240 and perform a series of actions. For example, an episode may merely be a loss of battery power at the power source 232 or the energy storage module 222, or one or more electrodes (e.g., ECG electrodes, defibrillation electrodes) may have lost connection. In such instances, the action module 242 may trigger an alert to the patient or to an outside source of the present situation. This may include activating an alert module. If an episode is a health risk, such as a cardiac event, the action module 242 may begin a series of steps. This may include issuing a warning to the patient, issuing a warning to a third party, priming the energy storage module 222 for defibrillation, releasing one or more conductive fluids proximate defibrillation electrodes 114, 116, and the like.

Figure 3:
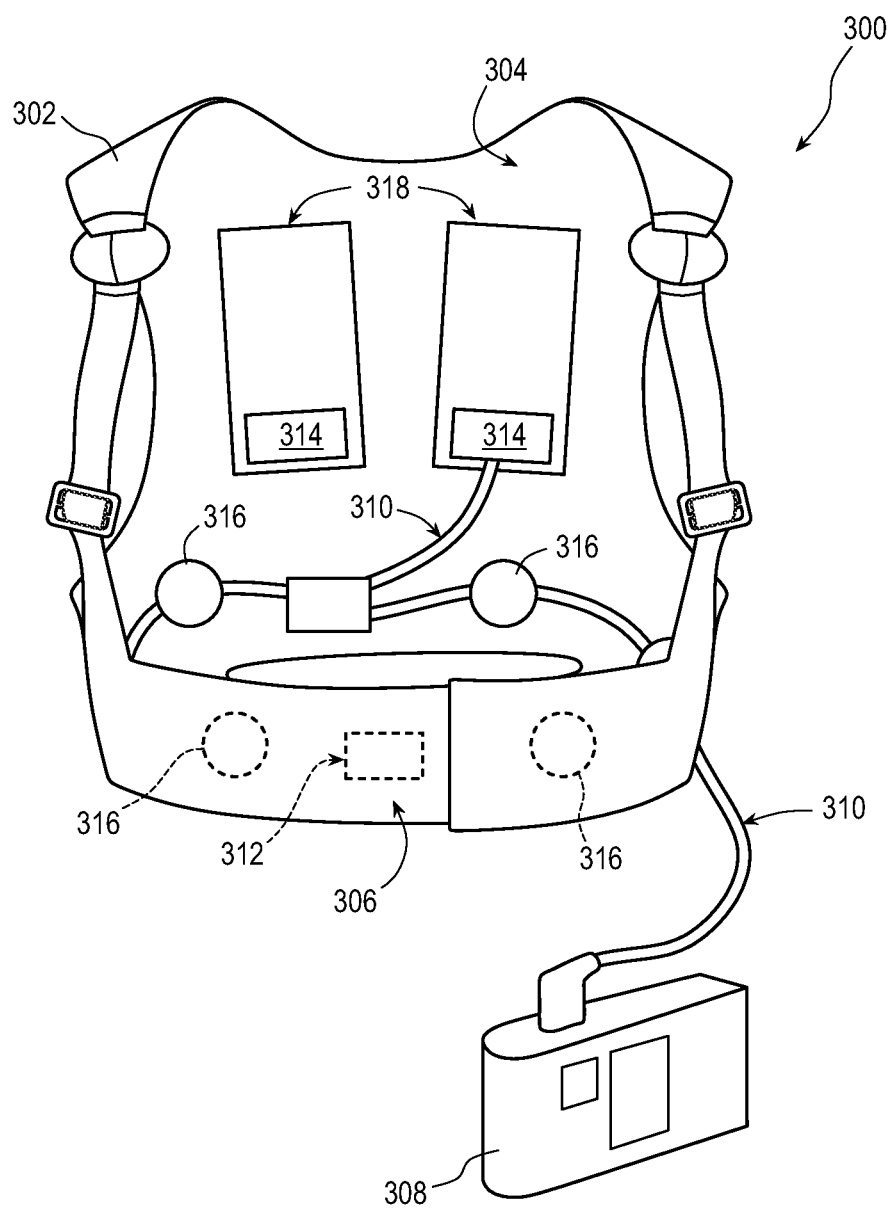
FIG. 3 is a diagram of sample embodiments of components of a WCD system in accordance with exemplary embodiments described herein.

FIG. 3 is a diagram of sample embodiments of components of a WCD system 300 according to exemplary embodiments. The WCD system 300 may be an example of the WCD system 104 describe with reference to FIG. 1. In some embodiments, the WCD system 300 may include a support structure 302 comprising a vest-like wearable garment. In some embodiments, the support structure 302 has a back side 304, and a front side 306 that closes in front of a chest of the patient.

In some embodiments, the WCD system 300 may also include an external defibrillator 308. The external defibrillator 308 may be an example of the defibrillator 108 describe with reference to FIGS. 1 and 2. As illustrated, FIG. 3 does not show any support for the external defibrillator 308, but as discussed, the defibrillator 308 may be carried in a purse, on a belt, by a strap over the shoulder, and the like as discussed previously. One or more wires 310 may connect the external defibrillator 308 to one or more electrodes 312, 314, 316. Of the connected electrodes, electrodes 312, 314 are defibrillation electrodes, and electrodes 316 are ECG sensing electrodes.

The support structure 302 is worn by the patient to maintain electrodes 312, 314, 316 on a body of the patient. For example, the back-defibrillation electrodes 314 are maintained in pockets 318. In some embodiments, the inside of the pockets 318 may comprise loose netting, so that the electrodes 314 can contact the back of the patient. In some instances, a conductive fluid may be deployed to increase connectivity. Additionally, in some embodiments, sensing electrodes 316 are maintained in positions that surround the patient's torso, for sensing ECG signals and/or the impedance of the patient.

In some instances, the ECG signals in a WCD system 300 may comprise too much electrical noise to be useful. To ameliorate the problem, multiple ECG sensing electrodes 316 are provided, for presenting many options to the processor (e.g., processor 202, FIG. 2). The multiple ECG sensing electrodes 316 provide different vectors for sensing the ECG signal of the patient.

Figure 4:
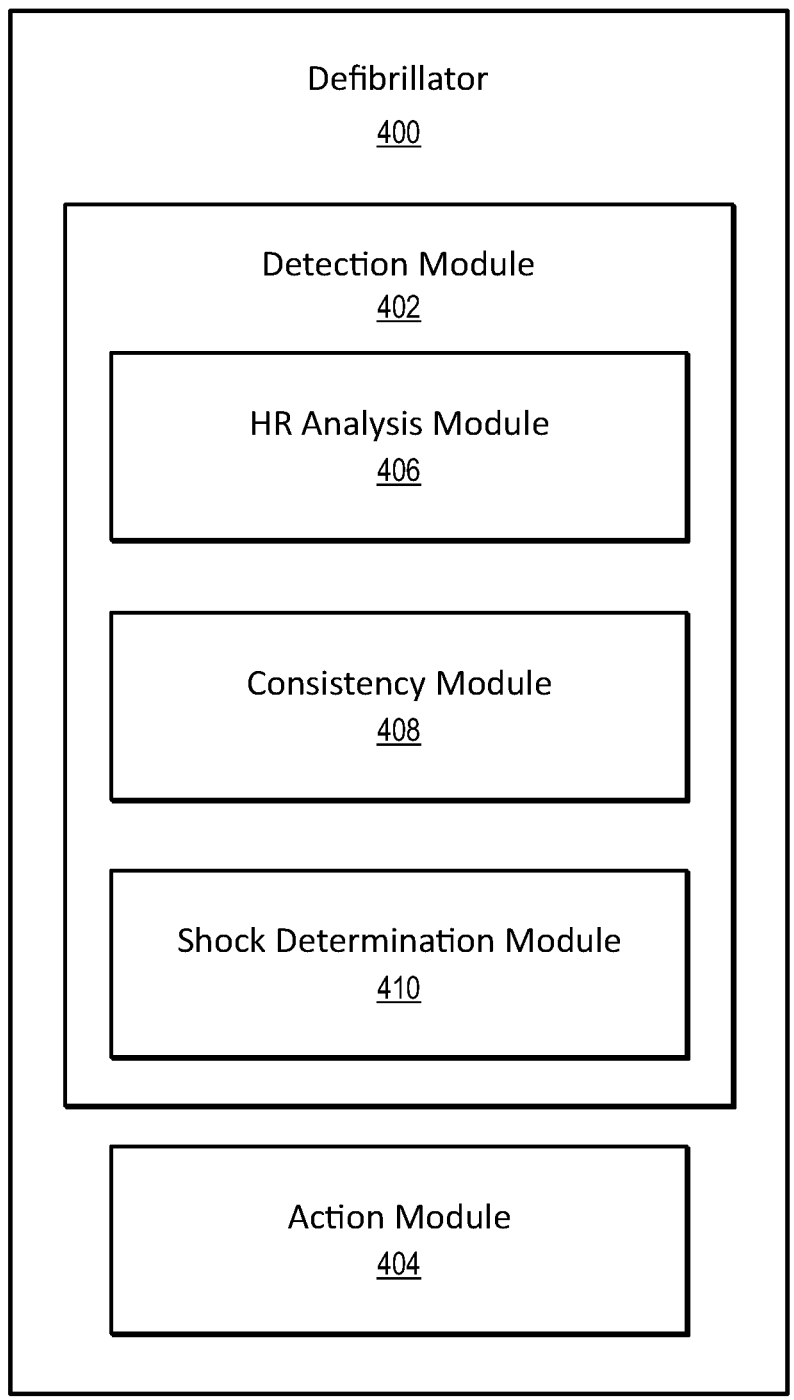
FIG. 4 is a block diagram of an example defibrillator in accordance with exemplary embodiments described herein.

FIG. 4 is a block diagram illustrating components of one example of a defibrillator 400. The defibrillator 400 may be an example of the defibrillator 108 described with reference to FIGS. 1 and 2 and defibrillator 308 described with reference to FIG. 3. In this example, the defibrillator 400 has a detection module 402 and an action module 404. The detection module 402 and action module 404 may be examples of the detection module 240 and action module 242 described with reference to FIG. 2. In some embodiments, the detection module 402 may include a heart rate (HR) analysis module 406, a consistency module 408, and shock determination module 410.

The detection module 402 may aid in the detection of slow PVT. For example, the shock determination module 410 may use data from one or both the HR analysis module 406 and the consistency module 408 to make a shock, delay shock, or no shock decision. These modules may also identify a slow PVT condition which may require a shock decision.

For example, the heart rate analysis module 406 may receive and analyze various heart rate signals from the patient. The heart rate analysis module 406 may receive various signals from the ECG inputs (e.g., the ECG electrodes 230, FIG. 2) and decipher the signals into various pieces of data including a QRS width and BPM. In some embodiments, the QRS width is the same as an R-wave width or duration. Other methods of assessing the duration of a complex should also be considered equivalent to QRS width. Specific thresholds may need to be adjusted for different metrics. QRS width may also be called an SVT discriminator. Throughout this disclosure, the use of QRS width and SVT discriminator are considered synonymous.

The heart rate analysis module 406 may analyze this information to define various heart rate ranges including a no shock, VT, and VF range. In some embodiments, these ranges may be specific to a particular patient. In other embodiments, these ranges may be fairly standard. The zones may also have other nuanced zones including a narrow VT range that may create a delay shock or watch condition. The zones may also include a slow PVT zone. This may be a zone where a shockable condition is occurring, but the condition is out of the range of normal shockable conditions. In some embodiments, the slow PVT zone is a based at least in part on beats per minute, beats per second, QRS width, QRS similarity, or some combination thereof.

In some embodiments, the heart rate analysis module 406 may determine the no shock threshold based at least in part on one or more of an expected accuracy of the heart rate detection algorithm, a maximum acceptable rate of false no shock classifications, a maximum acceptable rate of false VT classifications, age and/or health of a patient, and the like. For example, the heart rate analysis module 406 may increase or decrease the heart rate threshold for no shock determination. The changes in the heart rate thresholds for no shock may carefully avoid an increased risk of improperly classifying the heart rate. These characteristics may be determined empirically from testing on known ECG database(s) or from analysis of clinical studies that assess the impact of the different rate thresholds on survival or some combination thereof. For particular patients, the heart rate analysis module 406 may adjust rate threshold from a standard threshold based on the patient's health or age or both. For example, a young, healthy patient may tolerate higher rates and benefit from a higher threshold, while an older or frail patient may benefit from a lower threshold.

Similarly, the heart rate analysis module 406 may analyze the heart rate and determine the threshold between the VT and VF classifications for each patient. The threshold between VT and VF may be based at least in part on the expected accuracy of the heart rate detection algorithm, the maximum acceptable rate of false VT classifications, the maximum acceptable rate of false VF classifications, and the like. The heart rate classifications may be based on BPM as discussed previously. Additionally, the heart rate analysis module 406 may include other zones such as a slow PVT zone, a narrow VT zone, narrow QRS complexes, and the like.

In some embodiments, the shock determination module 410 may also use QRS information to make a shock determination. The shock determination module 410 may receive QRS information from the HR analysis module 406. For example, the heart rate analysis module 406 may also analyze QRS width to contribute to the shock, delay shock, no shock determination. For example, a QRS width of less than 120 microseconds (ms) may indicate no shock is necessary. A QRS width of greater than 120 ms can indicate the presence of either VT or VF.

In some embodiments, the HR analysis module 406 may also determine a VF width which may contribute to the shock determination. The VF width, as used herein, is used to refer to the measured width of complexes detected during VF. The VF width is a function of the heart rate and QRS width, bounded by the "no shock" heart rate threshold and the "VF" heart rate threshold. In some embodiments, the VF width may be calculated using the following equation:

$$\text{Index}=-39+(0.14*\text{Heart Rate})+(0.13*\text{QRS Width})$$

A rhythm with a positive index is classified as "VF" because it might be VF, but a rhythm with wide complexes and a negative index is classified as "VT" because it is unlikely to be VF based on empirical study of known ECG data.

In some embodiments, the consistency module 408 may also be used to determine a shock determination by calculating a consistency metric. The consistency metric is a calculation of the consistency between a specific QRS complex and a standard QRS complex for a specific patient. For instance, the consistency module 408 may analyze the heart rhythm to determine how organized, or similar, the heart rhythm is between beats. If the patient has a disorganized rhythm, the patient is likely experiencing VF and may require a shock. If the patient has an organized rhythm, the patient is likely experiencing VT and does need shock therapy.

In some embodiments, the consistency module 408 may determine the QRS morphology. For example, the consistency module 408 may analyze the QRS complexes and determine if the QRS complexes are consistent or organized from beat to beat. A consistent or organized rhythm has a similar QRS morphology from beat to beat. In contrast, an inconsistent or disorganized rhythm has a QRS morphology with beat-to-beat variations.

In one embodiment, the consistency module 408 may determine a typical or standard QRS complex by averaging a large number of previous detected complexes together. Additionally, the consistency module 408 may determine a consistency metric by comparting a current QRS complex to the calculated typical QRS complex for a specific patient. In some embodiments, the consistency module 408 sets the standard QRS complex for each patient by examining a predetermined number of QRS complexes from a single channel or vector.

Figure 6:
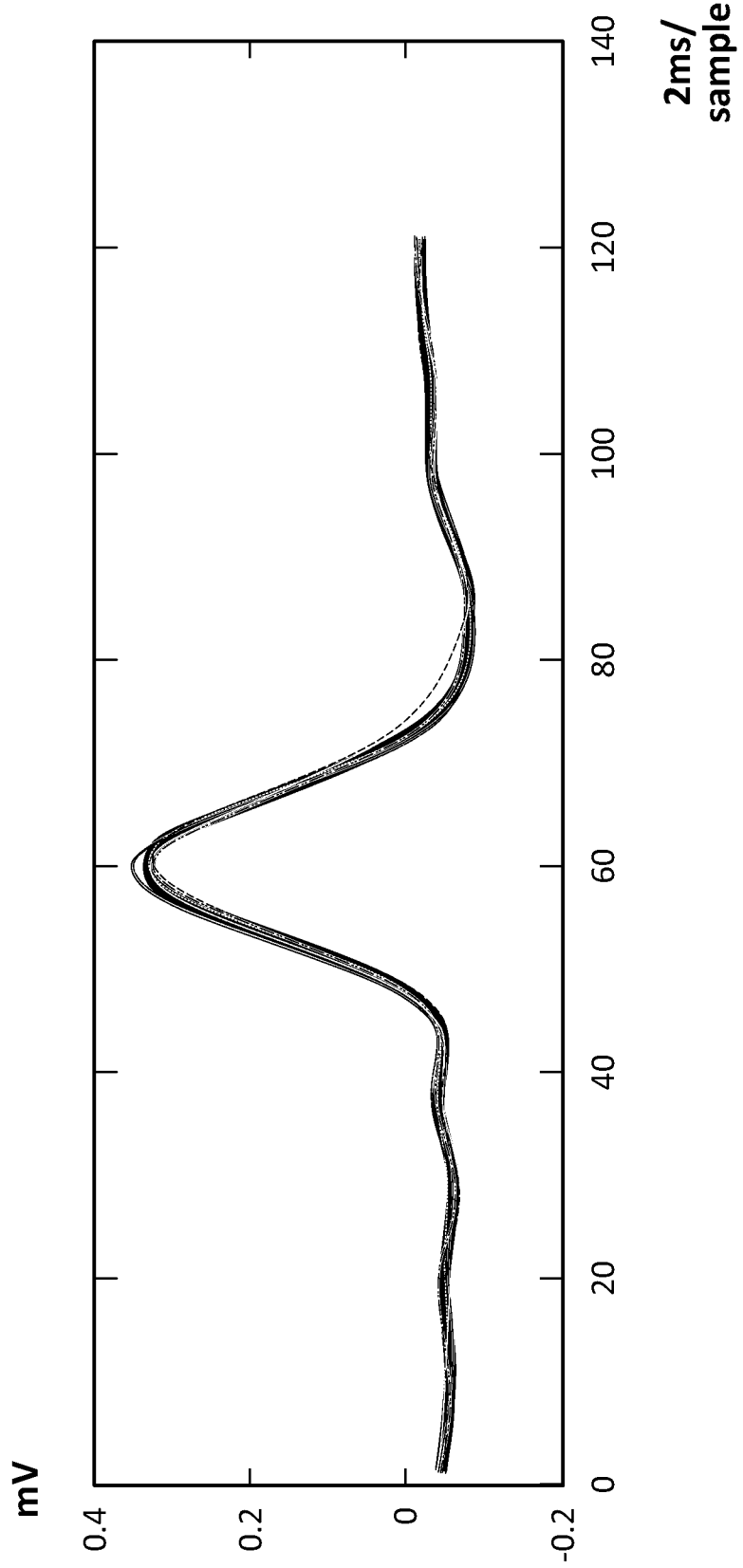
FIG. 6 is exemplary QRS complex similarity according to exemplary embodiments described herein.

As shown in FIG. 6, QRS complexes with a normal rhythm have a relatively high consistency. Referring back to FIG. 4, the consistency module 408 may utilize QRS complexes from a predetermined segment to determine the QRS standard. The predetermined segment may be between 3 and 8 seconds, and in some embodiments may be approximately 4.8 seconds. The QRS complexes may be averaged to determine a template. In some embodiments, the consistency module 408 uses N QRS complexes to develop the standard. The consistency module may set N at a fixed number such that the QRS complex is a rolling average of the most N complexes. For example, if N is set to eight (8), the consistency module 408 may use the most recent eight (8) QRS complexes and then signal average those complexes to determine the template. In another embodiment, N may be set to a time duration, such as ten (10) seconds. In this embodiment, the consistency module 408 may signal average the QRS complexes over the previous time duration, ten (10) seconds in this example.

The consistency module 408 may determine the QRS signal average using various methods. For example, in one embodiment, the consistency module 408 may apply a least mean squares (LMS) algorithm. In another embodiment, the consistency module 408 may use a recursive least squares filter (RLS) algorithm. In further embodiments, the consistency module 408 may use other methods and algorithms to determine the QRS signal average. In still further embodiments, the consistency module may determine the QRS template as described in U.S. patent application Ser. No. 16/366,313, incorporated herein in its entirety.

Once the QRS template or standard is set, the consistency module 408 may then determine a QRS consistency metric by comparing and calculating the consistency or similarity between a given QRS complex and a the standard QRS complex for a patient. The QRS similarity is used to calculate a consistency metric used by the shock determination module 410 to distinguish between VF, VT, MVT, PVT, or other shockable or non-shockable conditions. The consistency module 408 may determine the consistency metric in one of several ways. For example, in one embodiment, the consistency module 408 may apply a cross-correlation algorithm to a received QRS complex and the standard QRS complex. In another embodiment, the consistency module 408 may apply an FFT spectral comparison algorithm to the received QRS complex and the standard QRS complex. In some embodiments, the consistency module 408 may calculate the consistency metric by determining the mean square error or mean absolute error between the received QRS complex and the QRS template. In some instances, the constituency module 408 may need to align the signals to determine these calculations. In yet another embodiment, the consistency module 408 may implement a match filter derived the QRS template. In yet another embodiment, the consistency module 408 apply one, more than one, another known method, or some combination of the various methods.

In embodiments, the shock determination module 410 is configured to receive the heart rate and QRS outputs from the HR analysis module 406 and consistency metric from the consistency module 408 and output a shock, delay shock, or no shock decision. For example, in some embodiments the shock determination module 410 will not issue a shock when the heart rate or the QRS output or both indicate a shock is not required and that the patient is healthy and functioning properly. Alternatively, the shock determination module 410 if the heart rate output indicates VF, the detection module 402 may output a shock decision. In another embodiment, if the heart rate output indicates VT, the detection module may output a no shock decision.

In further embodiments, the shock determination module 410 may delay a shock determination when the HR analysis module 406 indicates VT is present. This may enable the heartrate to normalize on its own and for the VT condition to self-terminate. If the VT condition does not self-terminate within a predetermined time delay period, the HR analysis module 406 may indicate the continued VT condition and the shock determination module 410 may change its determination to a "shock" decision. In some embodiments, the predetermined time delay period may be between approximately five seconds and approximately two minutes. In another embodiment, the predetermined time delay period may be approximately forty-five (45) seconds to allow the VT condition to self-terminate.

In some embodiments, the shock determination module 410 may tailor the shock determination to a particular patient. For example, in some embodiments, the shock determination module 410 may issue a shock determination for ECGs having a heart rate and QRS width above the VF Width. In another example, the shock determination module 410 may issue a no shock decision for ECGs having a heart rate and QRS width that is below the VF Width. In another example, the shock determination module 410 may issue a delay shock decision, for ECGs having a heart rate and QRS width that is below the VF Width. The delay shock decision may allow a VT rhythm to self-terminate as described previously.

In some embodiments, the shock determination module 410 may use one or more tables or graphs to make a shock determination. In one embodiment, the table below summarizes an example HR and QRS widths that can define no Shock, VT, VF, and PVT zones.

TABLE 1

| No Shock, VT, and VF Zones | | | | |
| --- | --- | --- | --- | --- |
| Parameter | No Shock | VT | VF | PVT |
| Heart Rate | <170 BPM | >170 BPM | >200 BPM | 120-170 BPM |
| QRS Width | <120 mS | >120 mS | >120 mS | >120 ms |

Figure 5:
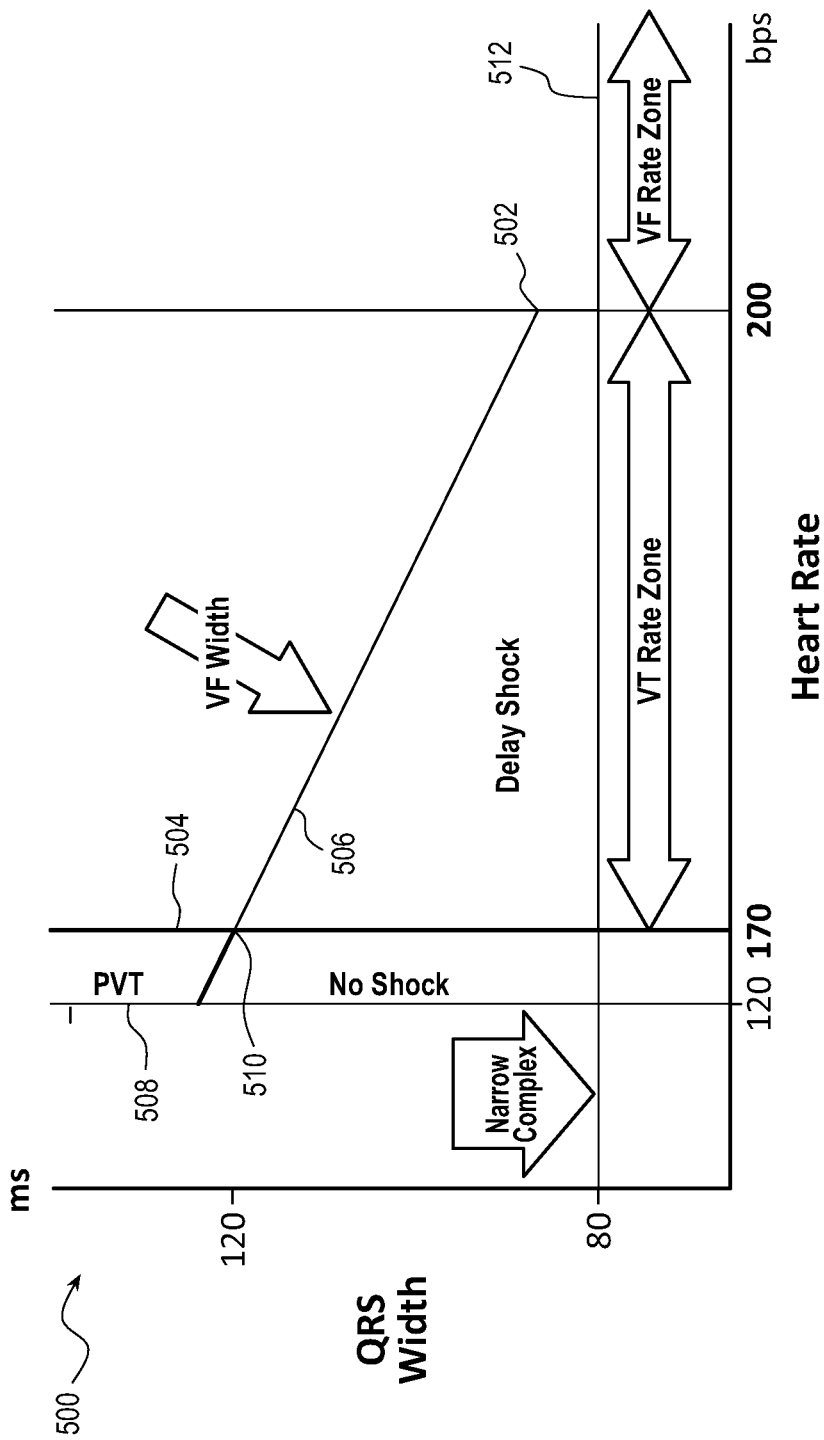
FIG. 5 is a graphical representation of different heart rate zones according to exemplary embodiments described herein.

In some embodiments, the shock determination module 410 may also use the VF width to determine shock, no shock, and delay shock zones. As shown in FIG. 5, a VF width as determined by the HR rate analysis module 406 defines a "VT/VF zone" between 170 BPS and 200 BPS. In this example, the VF Width is a linear function 506 from point 510 (170 BPS, 120 ms) to point 502 (200 BPS, 84.6 ms). In other embodiments different functions can be used, including non-linear functions wherein the VF Width in general decreases in QRS width as the heart rate increases within the VT/VF zone.

However, these standard values for VF and VT may, in some cases, ignore PVT or slow PVT as it is sometimes called. However, studies have shown that patients can experience a shockable condition when their BPM is low but their QRS width is high. This condition doesn't register under normal cut-offs and therefor has its own zone. In some embodiments this "slow PVT" region depicted is used as a monitoring zone. Rhythms that met defined duration criteria may trigger an episode that can be later reviewed by clinicians, researchers, and/or other medical personnel. By triggering episodes only for the slow PVT rhythms and not all rhythms above 120 BPM, the action module 404 may avoid storing unnecessary episodes triggered by noise or relatively normal rhythms.

Along with the QRS width and heart rate information, in some embodiments, the shock determination module 410 may also use the consistency metric in outputting a shock/no shock decision according to embodiments. For example, a rhythm having heart rate and QRS width above the VF Width in FIG. 5 could be VF, or PVT or MVT as described above in the Heart Rate/QRS Width Embodiments section.

The action module 404 may take one or more various actions based at least in part on data from the detection module 402. For example, the action module 404 may issue a shock command, a no shock command, or a delay shock command. In some embodiments, the action module 404 may issue one or more warnings to a patient concerning the shock, no shock, delay shock command. In some instances, the action module 404 may store episode data in a memory.

The episode data may include any abnormal heart rhythms including slow PVT or other shockable conditions. The episode data may also include further data that may require further analysis.

Figure 7:
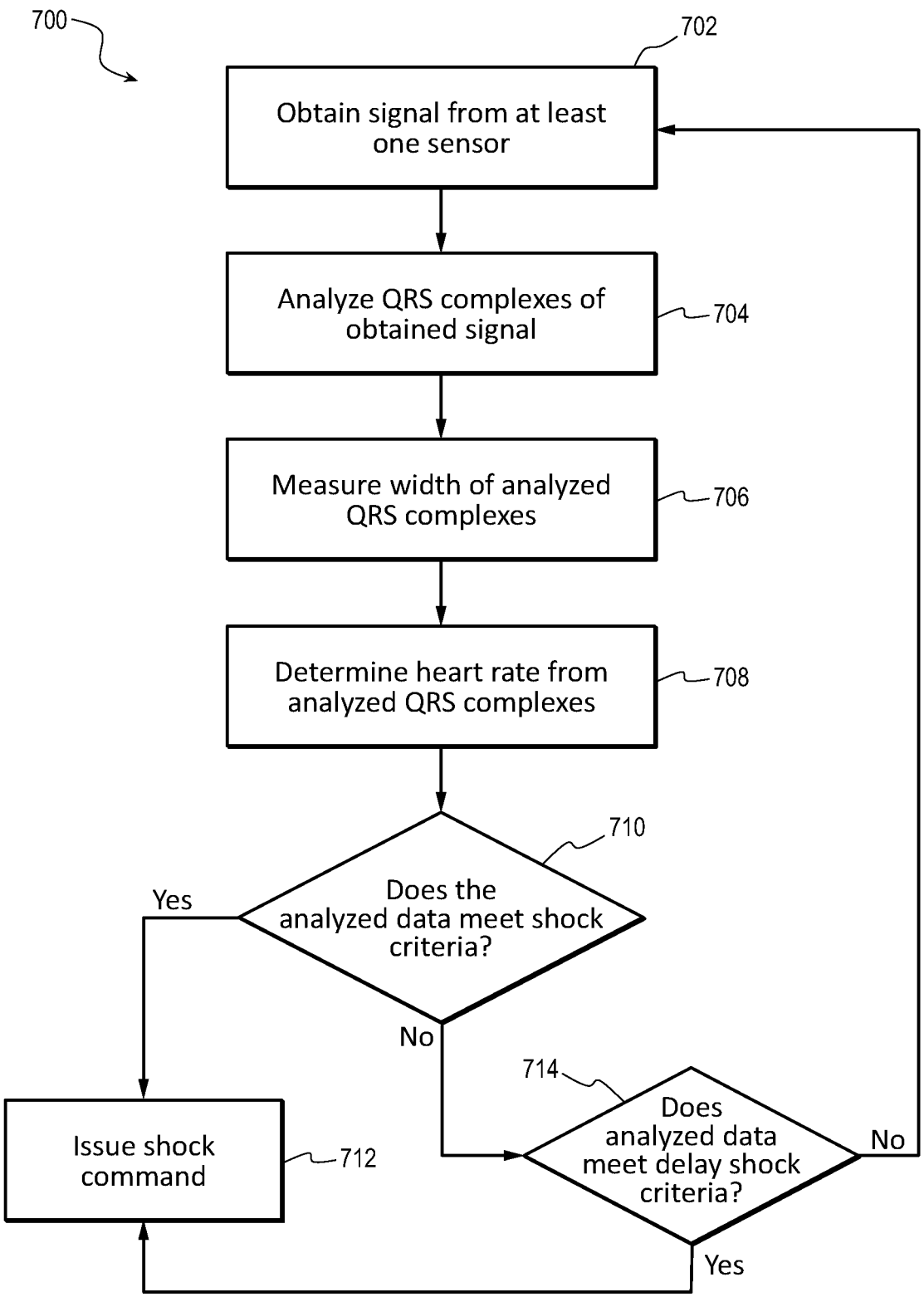
FIG. 7 is a flow diagram in accordance with exemplary embodiments described herein.

FIG. 7 is a flow chart illustrating an example of a method 700 for WCD systems, in accordance with various aspects of the present disclosure. For clarity, the method 600 is described below with reference to aspects of one or more of the systems described herein.

At block 702, the method 700 include obtaining a signal from at least one sensor. The sensor may include a motion sensor, one or more ECG electrodes, and the like. The signal may comprise various types of signals. For example, the motion sensor may detect a patient movement including steps over time. The ECG electrodes may a patient's ECG signal. In some embodiments, the ECG electrodes may record electrical activity generated by heart muscle depolarization. In some embodiments, the method 700 may receive more than one signal from the same type of sensor. For example, the method 700 may receive up to four signals from four separate ECG electrodes. Similarly, the patient may have multiple motion sensors and the like.

At bock 704, the method 700 may analyze the data from the at least one sensor into usable data. For example, the method 700 may analyze the QRS complexes of the obtained signal. In some embodiments, analyzing the signal may include filtering through the raw signal to remove any noise in the system. In further embodiments, the signal may be analyzed to determine a heart rate over time, a heart rate histogram, steps over time, detected ECG arrhythmias, wearability data, heartrate irregularities, QRS data, and the like. In some embodiments, the method 700 may parse the signal to differentiate between QRS signals.

At block 706, the method 700 may determine a width of the analyzed QRS complexes. In some embodiments, the analyzed width of the QRS complexes may be used to determine a QRS consistency metric as discussed previously. In further embodiments, the method 700 may compare a specific QRS width to a QRS consistency metric to determine if the patient is experiencing any abnormalities or concerning or shockable conditions. Further, at block 708, the method 700 may determine a heart rate of the patient from the analyzed QRS complexes.

Then, at block 710, the method 700 may determine if the analyzed data meets any shock criteria. For example, the method 700 may determine if the patient is experiencing VF or VT. The method 700 may also determine if the patient is experiencing other heart conditions such as slow PVT. In some embodiments, the method 700 may analyze the QRS width and the heart rate to determine if the patient is experiencing slow PVT. In other embodiments, the method 700 may alternatively or additionally use the VF width to determine if the patient has a shockable condition. The VF width, discussed previously, may provide another factor to determine which heart condition the patient is experiencing. In still further embodiments, the method 700 may additionally or alternatively use the QRS width and consistency metric to determine a shockable condition.

If the patient is experiencing a shockable condition, including slow PVT, then at block 712, the method 700 may issue a shock command. If the patient is not experiencing a shockable condition, then the method 700 may, at block 714, determine if the analyzed data meets a delay shock condition. If the patient is experiencing a delay shock condition, the patient may be closely monitored to determine if the condition expires or resolves itself or, at block 712, if the condition continues, the method 700 may issue a shock command. Alternatively, if the delay shock criteria is not met, then the method 700 may continue to reanalyze the patient's heart rate at block 702 by once again obtaining a signal from at least one sensor.

Thus, the method 700 may provide for one method of analyzing a patient's heart rate for shockable conditions. It should be noted that the method 700 is just one implementation and that the operations of the method 700 may be rearranged or otherwise modified such that other implementations are possible.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method for controlling a wearable cardioverter defibrillator (WCD), the method comprising:
    obtaining a signal from at least one sensor, wherein the at least one sensor gathers data about a patient to generate the signal;
    analyzing the signal from the at least one sensor into QRS complexes;
    determining a width of the QRS complexes;
    determining a heart rate from the width of the QRS complexes;
    detecting a slow polymorphic ventricular tachycardia (PVT) episode has occurred in the patient based, at least in part, on the heart rate and QRS complexes, the detected slow PVT episode comprises detecting that the heart rate is between 120 and 170 Beats per Minute (BPM) and the QRS complexes are wider than 120 ms;
    classifying the slow PVT episode as a delay shock condition or a no shock condition;
    detecting whether the delay shock condition has continued for a predetermined period after the slow PVT episode was detected; and
    issuing a shock command to the WCD in response to a detection that the delay shock condition has continued for the predetermined period, wherein the shock command causes the WCD to deliver a shock to the patient.

2. The method of claim 1, further comprising:
    not providing any therapy during the predetermined period.

3. The method of claim 1, further comprising:
    calculating a QRS consistency metric for the patient;
    comparing a QRS width to the QRS consistency metric; and
    calculating a similarity between the QRS width and the QRS consistency metric,
    wherein the slow PVT episode is classified as the delay shock condition based on the similarity.

4. The method of claim 1, wherein the predetermined period is between 5 seconds and 120 seconds.

5. The method of claim 1, wherein in response to the slow PVT episode being classified as the delay shock condition, the WCD is configured to issue a delay shock command that causes the WCD to wait for the predetermined period prior to delivering the shock to the patient.

6. The method of claim 5, further comprising:
    monitoring the heart rate for the predetermined period; and
    wherein the issuing of the shock command is based, at least in part, on the heart rate monitored during the predetermined period.

7. The method of claim 1, wherein the predetermined period comprises a time period between five seconds and two minutes.

8. A wearable cardioverter defibrillator (WCD) system configured to be worn by a patient, the system comprising:
    at least one sensor positioned to gather data about the patient;
    one or more memories to store patient data; and
    a processor that is communicatively coupled to the at least one sensor and the one or more memories, wherein the processor is configured to:
    obtain a signal from the at least one sensor, wherein the signal is generated by the sensor based, at least in part, on the data gathered about the patient;
    analyze the signal from the at least one sensor to detect QRS complexes in a heart rhythm of the patient,
    determine a width of the QRS complexes,
    determine a heart rate from intervals between the QRS complexes,
    detect a slow polymorphic ventricular tachycardia (PVT) episode has occurred in the patient based, at least in part, on the heart rate and width of QRS complexes, the detected slow PVT episode comprises detecting that the heart rate is between 120 and 170 Beats Per Minute (BPM) and the widths of QRS complexes are wider than 120 ms,
    classify the slow PVT episode as a delay shock condition or a no shock condition; and
    in response to a detection that the delay shock condition continued for a predetermined period, issue a shock command to the WCD, wherein the shock command causes the WCD to deliver a shock to the patient.

9. The system of claim 8, wherein the processor is further configured to:
    not provide any therapy during the predetermined period.

10. The system of claim 8, wherein the processor is further configured to:
  calculate a QRS consistency metric for the patient;
  compare a QRS width to the QRS consistency metric; and
  calculate a similarity between the QRS width and the QRS consistency metric, wherein the slow PVT episode is classified as the delay shock condition based on the similarity.

11. The system of claim 8, wherein the predetermined period is between 5 seconds and 120 seconds.

12. The system of claim 8, wherein in response to the slow PVT episode being classified as the delay shock condition, the processor is configured to issue a delay shock command that causes the WCD to wait for the predetermined period prior to delivering the shock to the patient.

13. The system of claim 12, wherein the processor is further configured to:
  monitor the heart rate for the predetermined period; and
  wherein the shock command is issued based, at least in part, on the heart rate monitored during the predetermined period.

14. The system of claim 8, wherein the predetermined period comprises a time period between five seconds and two minutes.

15. A method for controlling a wearable cardioverter defibrillator (WCD), the method comprising:
  obtaining a signal from at least one sensor, wherein the at least one sensor gathers data about a patient to generate the signal;
  calculating a measured heart rate and a consistency metric from the signal;
  determining whether the measured heart rate satisfies a heart rate threshold;
  determining whether the consistency metric satisfies a consistency threshold;
  detecting a slow polymorphic ventricular tachycardia (PVT) episode has occurred in the patient based at least in part on the heart rate threshold and consistency threshold being satisfied, the detected slow PVT episode comprises detecting that a heart rate is between 120 and 170 Beats Per Minute (BPM) and widths of QRS complexes are wider than 120 ms;
  classifying the slow PVT episode as a delay shock condition or a no shock condition based at least in part on the consistency metric;
  detecting whether the delay shock condition has continued for a predetermined period after the slow PVT episode was detected; and
  issuing a shock command to the WCD in response to detection that the delay shock condition continued for the predetermined period, wherein the shock command causes the WCD to deliver a shock to the patient.

16. The method of claim 15, further comprising:
  monitoring the measured heart rate for the predetermined period; and
  selectively canceling the shock of the patient based on the measured heart rate monitored during the predetermined period.

17. The method of claim 15, wherein the consistency metric is a Supraventricular tachycardia (SVT) discriminator consistency metric for the patient.

18. The method of claim 17, wherein the consistency metric is determined by:
  calculating a SVT discriminator from the signal;
  comparing the SVT discriminator to the SVT discriminator consistency metric; and
  calculating a similarity between the SVT discriminator and the SVT discriminator consistency metric.

19. The method of claim 15, further comprising:
  not providing any therapy during the predetermined period.

20. The method of claim 15, wherein in response to the slow PVT episode being classified as the delay shock condition, the WCD is configured to issue a delay shock command that causes the WCD to wait for the predetermined period prior to delivering the shock to the patient.

21. The method of claim 15, wherein the predetermined period comprises a time period between five seconds and two minutes.

* * * * *